United States Patent [19]

Dudeck et al.

[11] 4,235,823

[45] Nov. 25, 1980

[54] PREPARATION OF DIKETONES

[75] Inventors: Christian Dudeck, Limburgerhof; Gunter Lehmann, Ludwigshafen; Karl-Heinz Ross, Mutterstadt; Werner Fliege, Otterstadt; Norbert Petri, Frankenthal; Hans Diem, Mannheim; Bernd Meissner, Heidelberg; Wolfgang Sauer, Mannheim, all of Fed. Rep. of Germany

[73] Assignee: BASF Aktiengesellschaft, Fed. Rep. of Germany

[21] Appl. No.: 52,103

[22] Filed: Jun. 26, 1979

[30] Foreign Application Priority Data

Jul. 15, 1978 [DE] Fed. Rep. of Germany ....... 2831229

[51] Int. Cl.³ ............................................. C07C 45/39
[52] U.S. Cl. .................... 568/402; 252/476; 568/412; 568/413
[58] Field of Search ............... 260/586 P, 593 R, 596, 260/603 C

[56] References Cited

U.S. PATENT DOCUMENTS

| 2,339,282 | 1/1944 | McNamee et al. | 260/596 |
|---|---|---|---|
| 2,339,346 | 1/1944 | McNamee et al. | 260/596 |
| 2,339,348 | 1/1944 | McNamee et al. | 260/596 |
| 3,941,811 | 3/1976 | Vegnav | 260/586 P |
| 3,948,997 | 4/1976 | Howe et al. | 260/596 |
| 3,959,383 | 5/1976 | Northeimer | 260/603 C |
| 4,076,754 | 2/1978 | Kiser et al. | 260/603 C |

FOREIGN PATENT DOCUMENTS

| 1032732 | 11/1955 | Fed. Rep. of Germany | 260/603 C |
|---|---|---|---|
| 2634439 | 2/1977 | Fed. Rep. of Germany | 260/603 C |
| 136352 | 3/1960 | U.S.S.R. | 260/603 C |

OTHER PUBLICATIONS

Trecek et al., Chem. Abst., vol. 86, #189,204; (1977).
Zhinkin et al., Proced. Acad. U.S.S.R., Chem. Ser., (1964) pp. 641-643.
Ullmans Encyk. der Tech. Chem., vol. 8, pp. 250-252.
Rappe et al., Annalen der Chemie, 596, p. 160 (1955).
Rappe et al., Tet. Letters, vol. 41, p. 3074 (1969).

*Primary Examiner*—Natalie Trousof
*Assistant Examiner*—James H. Reamer
*Attorney, Agent, or Firm*—Keil & Witherspoon

[57] ABSTRACT

Diketones are prepared by oxidizing glycols in the presence of a silver catalyst and/or copper catalyst of a specific particle size, under specific temperature conditions and with a specific composition of the catalyst. The end products are starting materials for the preparation of dyes, drugs, plastics, scents, wrinkle-resist finishes and assistants for increasing the tear strength and resilience of fibrous materials, hardeners for use in the photographic industry, textile assistants for preventing shrinkage after washing, and paper assistants.

12 Claims, No Drawings

PREPARATION OF DIKETONES

The present invention relates to a process for the preparation of diketones by oxidizing glycols in the presence of a silver catalyst and/or copper catalyst of a specific particle size, under specific temperature conditions and with a specific composition of the catalyst.

Ullmanns Encyklopädie der technischen Chemie, Volume 8, pages 250–252, discloses that one of the most important processes for the preparation of glyoxal is the oxidation of ethylene glycol with air. It states that the reaction is carried out at from 300° to 325° C., with copper oxide as the catalyst, and in the presence of halogen compounds. Absorption of the reaction mixture in a glyoxal solution or in water gives a 32 percent strength solution of glyoxal. A process of this type gives yields of at most 65 percent and space-time yields of only from 0.04 to 1.5 grams of glyoxal/cm$^3$ of catalyst volume per volume.

Proceed. Acad. Sci. USSR, Chem. Ser. (1964), pages 641–643, discloses the use of silver as a catalyst on a pumice or alumina carrier. Such catalysts are said to give only poor results and hence, silver spirals are preferred as catalysts. The best result is achieved with silver spirals, at 600° C., using a pressure of from 544 to 816 mbar; the yield is 69 percent. The end product is obtained in the form of a 25 percent strength by weight aqueous solution pf glyoxal, which additionally contains from 5 to 10 percent by weight of glycol. The data disclosed correspond to a residence time of 0.037 second and a space-time yield of 4.46 grams of glyoxal per hour per cm$^3$ of catalyst volume. An additional inert gas is not used. Working under reduced pressure is unsatisfactory from the point of view of the space-time yield.

Russian Pat. No. 136,352 describes the oxidation of glycol at from 500° to 700° C., using a catalyst of silver on alumina (containing 40% of Ag). Before use, the catalyst is heated for 2 hours at from 600° to 700° C. The flow rate is 2.1 meters per second. The starting mixture contains 40 percent of glycol and 60 percent of water. The yield is 61 percent and the space-time yield is 12.8 grams of glyoxal per hour per gram of catalyst. The process has the disadvantage that the preparation of the catalyst is involved and that a rather dilute glycol solution must be employed. When the catalyst is spent, for example due to poisoning, it has to be reprocessed by carrying out numerous chemical operations.

German Published Application DAS 1,032,732 discloses that when using copper and silver as the catalyst, a promoter, for example TiO$_2$ and Mo$_2$O$_5$, is required, and that to increase the yield an inhibitor, for example HCl, Cl$_2$ or ethylene dichloride, must be added. Under these conditions, the best result achieved is a space-time yield of 0.043 gram per cm$^3$ per hour. According to the same publication, the result can be improved if the silver is applied to a carrier of pumice, silica gel or alumina. The process is carried out at from 300° to 450° C., using an air/nitrogen mixture containing from 1.6 to 5 percent of oxygen. A yield of 55 percent and a space-time yield of 0.104 gram of glyoxal per cm$^3$ of reaction space per hour is achieved. This space-time yield is unsatisfactory.

German Laid-Open Application DOS 1,923,048 describes the preparation of glyoxal using a catalyst comprising two components (a and b), namely
(a) copper or silver and/or gold, together with
(b) germanium, tin, lead, nitrogen, phosphorus, arsenic, antimony and/or bismuth.

The use of silver in conjunction with tin, phosphorus and/or arsenic, and overall, the use of copper rather than silver, is preferred. A reaction temperature of about 180°–600° C., preferably about 300°–450° C., is quoted. Diluent gases can be used, preferably with a molar ratio of diluent gas to oxygen ranging from 5:1 to 200:1. Suitable residence times are from 0.1 to 20 seconds, times from 1 to 5 seconds being preferred. Whilst numerous Examples with copper catalysts are given, only one Example using a copper-free silver catalyst (silver/phosphorus) is described, and this is carried out at about 430°–450° C. The space-time yield calculated from the data is unsatisfactory. A further disadvantage is that the preparation of the catalyst is complicated.

German Laid-Open Application DOS 2,634,439 uses a catalyst which comprises phosphorus combined with Cu and/or Ag. A bromine compound is added to the reaction in an amount which suffices to increases the yield of glyoxal but is not so great that the glycol aldehyde formation is substantially increased or the conversion of the ethylene glycol drops to less than about 90 percent. An inert gas is added. In all the Examples, a copper/silver/phosphorus catalyst is used. The space-time yield is only 1.5 grams of glyoxal per cm$^3$ of catalyst per hour. A further disadvantage is that the catalyst can only be regenerated by involved methods.

Annalen der Chemie, 596 (1955), 160 discloses heating n-hexane-2,5-diol with a hydrogenation catalyst at about 150° C., giving up to 70 percent of hexan-2-ol-5-one, with elimination of hydrogen, whilst at higher temperatures up to 80 percent of acetonylacetone are obtained.

Tetrahedron Letters, 41 (1964), 3,074 discloses that hexane-2,5-diol is converted to 2,5-hexanedione, in 89 percent yield, by treatment with lead tetraacetate in pyridine at room temperature; the yield is not improved by raising the temperature. The product contains esters of acetic acid and unconverted alcohol. Reaction times of from 10 to 20 hours are required; the impurities make working-up difficult.

All the above processes are unsatisfactory from the point of view of simple and economical operation, simple preparation of the catalyst and good space-time yields.

We have found that diketone of the formula I

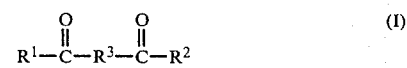

where R$^1$ and R$^2$ are identical or different and each is hydrogen or an aliphatic radical, R$^3$ is an aliphatic radical which may or may not be interrupted by —O— radicals and, if R$^1$ and/or R$^2$ is an aliphatic radical, may also be a single bond, is obtained in an advantageous manner by oxidizing a glycol with oxygen in the presence of a metal catalyst, if a glycol of the formula (II)

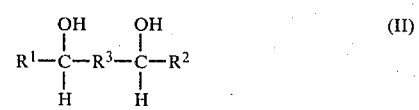

where R$^1$, R$^2$ and R$^3$ have the above meanings, is oxidized at from 450° to 750° C. in the presence of a catalyst comprising 2 or more layers of silver crystals and- /or copper crystals, some of the layers, accounting for from 70 to 95 percent by weight of the catalyst, containing particles of size from 0.75 to 2.5 mm, whilst the remainder of the layers, accounting for from 5 to 30 percent by weight of the catalyst, contain particles of size from 0.1 to 0.75 mm.

If hexane-2,5-dione is used, the reaction can be represented by the following equation:

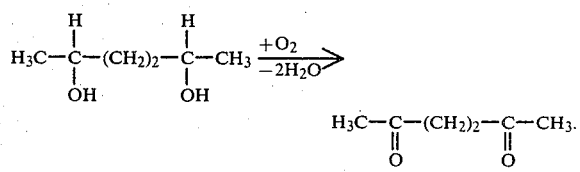

Compared to the conventional processes, the process according to the invention surprisingly gives, more simply and more economically, a better overall result in respect of yield and purity of the end product, and life of the catalyst. The space-time yield is relatively better. Involved preparation and processing of the catalyst are avoided.

Compared to the processes previously described, the catalyst according to the invention has a longer life and can be obtained more simply and more economically. Silver crystals of all particle sizes, as obtained from the electrolytic preparation of silver granules, can be used. Accordingly, in the process according to the invention the electrolysis equipment is better utilized and can be made of correspondingly smaller size; there is a saving in energy, operatives required and auxiliaries, for example nitric acid, and operations such as washing, screening and drying the silver are simplified. In the conventional processes, the silver must first be applied to the carrier or must be metered-in subsequently. Where silver spirals are used, these must be specially manufactured. All these advantageous results of the process according to the invention are surprising. In view of the prior art, it was not to be expected that by using pure silver crystals of a specific particle size, instead of silver spirals or silver on carriers or silver together with promoters (phosphorus), it would be possible to increase the rate of reaction and hence the space-time yield, and indeed to do so substantially.

Preferred starting materials II and accordingly preferred end products I are those where the radicals $R^1$ and $R^2$ are identical or different and each is hydrogen or alkyl of 1 to 8 carbon atoms, $R^3$ is alkylene of 1 to 8 carbon atoms or alkenylene or alkynylene of 2 to 8 carbon atoms, the chains of which alkylene, alkenylene and alkynylene radicals may be interrupted by 2 oxygen atoms or in particular one oxygen atom, and, if $R^1$ and/or $R^2$ is an aliphatic radical, $R^3$ may also be a single bond.

The above radicals may in addition be substituted by groups which are inert under the reaction conditions, for example alkyl of 1 to 4 carbon atoms.

Examples of suitable starting materials II are propane-1,2-diol, butane-1,2-diol, butane-1,3-diol, butane-1,4-diol, butane-2,3-diol, pentane-1,2-diol, pentane-1,3-diol, pentane-1,4-diol, pentane-1,5-diol, pentane-2,3-diol, pentane-2,4-diol, hexane-1,2-, -1,3-, -1,4-, -1,5-, -1,6-, -2,3-, -2,4-, -2,5- and -3,4-diol, heptane-1,2-, -1,3-, -1,4-, -1,5-, -1,6-, -1,7-, -2,3-, -2,4-, -2,5-, -2,6-, -3,4- and -3,5-diol, octane-1,2-, -1,3-, -1,4-, -1,5-, -1,6-, -1,7-, -1,8-, -2,3-, -2,4-, -2,5-, -2,6-, -2,7-, -3,4-, -3,5-, -3,6- and -4,5-diol, diethylene glycol, di-1,3-propylene glycol, di-1,2-propylene glycol, di-1,2-butylene glycol, di-1,3-butylene glycol and di-1,4-butylene glycol, but-2,3-ene-1,4-diol, pent-2,3-ene-1,5-diol, hex-2,3-ene-1,6-diol, hex-3,4-ene-1,6-diol, hept-2,3-ene-1,7-diol, hept-3,4-ene-1,7-diol, oct-2,3-ene-1,8-diol, oct-3,4-ene-1,8-diol, oct-4,5-ene-1,8-diol, but-2,3-yne-1,4-diol, pent-2,3-yne-1,5-diol, hex-2,3-yne-1,6-diol, hex-3,4-yne-1,6-diol, hept-2,3-yne-1,7-diol, hept-3,4-yne-1,7-diol, oct-2,3-yne-1,8-diol, oct-3,4-yne-1,8-diol and oct-4,5-yne-1,8-diol.

Advantageous starting materials for the process are compounds II by themselves or mixed with water or with an organic solvent which is inert under the reaction conditions; the aqueous mixtures can advantageously contain from 50 to 90 percent by weight, and the organic mixtures from 45 to 90 percent by weight, of starting material II. The latter is fed into the reaction chamber as vapor, which may or may not be mixed with steam or solvent vapor, and may or may not be mixed with inert gas. The oxidizing agents used may be pure oxygen or gases containing free oxygen, in particular air. Oxygen, preferably in the form of air, and the starting material II are advantageously used in a ratio of from 0.3 to 1.2, especially from 0.4 to 0.9, mole of oxygen per mole of starting material II. The air and inert gas, if any, can be introduced directly into the process of vaporization of the starting material II, advantageously into the boiling mixture of starting material II and water or solvent, or may be introduced at any other point upstream of the catalyst. The residence time in the reaction chamber is in general at most 0.2, appropriately from 0.0005 to 0.2, advantageously from 0.001 to 0.2, more particularly from 0.001 to 0.15 and preferably from 0.001 to 0.11 second. The residence time is based on, and calculated from, the volume of the reaction zone without catalyst packing. For example, the reaction space of an empty tubular reactor can serve as the basis of calculation.

The total thickness of the catalyst bed is advantageously from 10 to 50, preferably from 15 to 30, mm. The catalyst particles, in the form of silver crystals and/or copper crystals, are arranged in the advantageously vertical reactor in an upper and lower part of the total bed, according to particle size. The entire catalyst bed advantageously rests on a pre-heated silver or stainless steel grid. The starting mixture of vaporous starting material II and oxygen or air is in general passed downward through the reactor so that the upper layer (or upper layers) at the same time means the part of the bed which faces the starting mixture. In reactors of different construction, or with different flow of the starting mixture, all statements made in the description regarding the upper (lower) part of the catalyst apply, in their general sense, to the corresponding part of the catalyst which faces the starting mixture (faces the discharged reaction mixture); for example, in the case of horizontal reactors they apply to the front (rear) part of the catalyst. The lower part contains from 70 to 95, preferably from 80 to 90, percent by weight of all catalyst particles and the upper part from 5 to 30, preferably from 10 to 20, percent by weight of all catalyst particles. The particles in the lower part of the bed have sizes of from 0.75 to 2.5 mm and those in the upper part from 0.1 to 0.75 mm. Each part of the bed can comprise one or more layers, preferably 1, 2 or 3 layers. A catalyst with from 3 to 7 layers, especially with 3 or 4 layers, is preferred. Each of these layers differs from the other in respect of the particle size of the silver crystals and/or copper crystals and in most cases also in respect of the proportion by weight of the total catalyst accounted for by the particular layer.

If the upper part of the bed comprises 2 layers, its upper layer preferably accounts for from 0.5 to 29.5 percent by weight and has particles with a size of from 0.1 to 0.4 mm and its lower layer accounts for from 0.5 to 29.5 percent by weight and has particles with a size of from 0.4 to 0.75 mm. If the upper part of the bed comprises 3 layers, the following are preferred in respect of the proportion by weight of the total catalyst (the particle size being shown in parentheses): upper layer 0.5–29 percent by weight (0.1–0.4 mm); middle layer 0.5–29 percent by weight (0.4–0.6 mm); lower layer 0.5–29 percent by weight (0.6–0.75 mm). Accordingly, the following proportions by weight (the particle size being shown in parentheses) are preferred in the case of the lower part of the bed:

(a) 2 layers: upper layer 5–90 (0.75–1 mm) % by weight;
lower layer 5–90 (1.00–2.5 mm) % by weight.
(b) 3 layers: upper layer 5–85 (0.75–1 mm) % by weight;
middle layer 5–85 (1–1.5 mm) % by weight;
lower layer 5–85 (1.5–2.5 mm) % by weight.

In most cases, each individual layer is distributed uniformly, so that the thickness of the individual layer is constant over the entire cross-section of the layer. In that case, the thickness of the layer depends directly on the above proportions by weight of the total catalyst, and on the size of the particles. However, it is also possible to arrange all or several or advantageously one layer non-uniformly, for example to introduce the majority of the catalyst particles at the middle, at the sides or advantageously at the edge of the layer and accordingly only to distribute a smaller residual amount over the remainder of the layer.

A particularly advantageous catalyst has the following composition:

| Layer 1: (top) | 5–30% | by weight of the catalyst, with particles of size 0.1–0.75 mm |
| Layer 2: | 5–90% | by weight of the catalyst, with particles of size 0.75–1 mm |
| Layer 3: (bottom) | 5–90% | by weight of the catalyst, with particles of size 1–2.5 mm |

Advantageously, the throughput is from 0.2 to 3 t, in particular from 0.4 to 1.6 t, of vaporous starting material II per m² of catalyst bed cross-section per hour. For industrial operation, catalyst bed diameters of at least 0.1 meter, advantageously of from 0.2 to 3 meters, are preferred. Mixtures of silver and copper, and in particular silver crystals alone, are preferred.

The reaction is carried out at from 450° to 750° C., advantageously from 500° to 700° C., especially from 600° to 700° C., under atmospheric or superatmospheric pressure, in general at from 0.8 to 2 bar, preferably from 0.8 to 1.8 bar, especially from 1.05 to 1.5 bar, batchwise or, preferably, continuously.

The oxidation may be carried out as follows: the starting material II and water, if any, are introduced, separately or as a mixture, into a vaporizer, for example a falling-film vaporizer, and are vaporized therein. The gaseous mixture of vaporous starting material II, air, inert gas, if any, and steam, if any, is then passed, in the stated amounts, through the catalyst bed at the reaction temperature. It is advantageous to cool the reaction gases, leaving the catalyst zone, rapidly, for example to 20°–160° C. This condenses the greater part of the end product I. The cooled gas mixture is then advantageously fed to an absorption tower in which the residual end product I is washed out of the gas mixture, advantageously in counter-current, by means of a suitable solvent, such as dimethylformamide, dimethylsulfoxide, acetone, methanol or water or mixtures of these and/or a condensate from previous reactions. The end product I is then isolated from the condensate and the absorbates in the conventional manner, for example by distillation.

The end products I obtainable by the process of the invention are valuable starting materials for the preparation of dyes, drugs, plastics, scents, wrinkle-resist finishes, assistants for increasing the tear strength and resilience of fibrous materials, hardeners in the photographic industry, textile assistants for preventing shrinkage after washing, and paper assistants, for example for increasing the wet strength.

In the Examples which follow, parts are by weight.

EXAMPLE 1

An installation comprising a vaporizer and a vertical tubular reactor is used. The reactor possesses, at its top, an inlet for the vaporous starting mixture, and the reactor cover. The catalyst bed is located below the reactor top and below this, in turn, is a cooling zone. The reactor is connected to an absorption column.

A catalyst comprising 28 parts of silver crystals with the following characteristics is introduced into the reactor, the height of the bed being 20 mm:

|  | Proportion of the catalyst (% by weight) | Particle size (mm) |
|---|---|---|
| Layer 1 | 14.1 | 0.1–0.75 |
| Layer 2 | 5.9 | 0.75–1 |
| Layer 3 | 80 | 1–2.5 |

Per hour, a mixture of 254 parts of n-hexane-2,5-diol and 247 parts of air is fed to the vaporizer and vaporized therein. The vaporous starting mixture is then passed through the catalyst and reacted at 650° C. and 1.4 bar. The throughput is 0.8 t/m².h. The residence time, based on the empty tube, is 0.1 second. The gaseous reaction mixture is now cooled to 20° C. and is then washed with water. 210.3 parts per hour of n-hexane-2,5-dione of boiling point 191° C., corresponding to a yield of 84.2% of theory, are obtained in the form of a 49.6 percent strength by weight solution, together with 6.8 parts of hexan-2-ol-5-one; there is no unconverted n-hexane-2,5-diol. The space-time yield is 33.4 g/cm³.h. The catalyst life is 125 days and the conversion is 100 percent.

EXAMPLE 2

The same installation as in Example 1 is used. A catalyst comprising 28 parts of silver crystals with the following characteristics is introduced into the reactor, the height of the bed being 20 mm:

|  | Proportion of the catalyst (% by weight) | Particle size (mm) |
|---|---|---|
| Layer 1 | 18.5 | 0.1–0.75 |
| Layer 2 | 81.5 | 0.75–2.5 |

Per hour, a mixture of 314 parts of n-hexane-2,5-diol and 212 parts of air is fed to the vaporizer and vaporized therein. The vaporous starting mixture is then passed through the catalyst and reacted at 600° C. and 1.4 bar. The throughput is 1 t/m².h. The residence time, based on the empty tube, is 0.1 second. The gaseous reaction mixture is now cooled to 20° C. and is then washed with water. 250 parts per hour of n-hexane-2,5-dione of boiling point 191° C., corresponding to a yield of 81 percent of theory, are obtained in the form of a 50.8 percent strength by weight solution, in addition to 4 parts per hour of unconverted n-hexane-2,5-diol and 17.7 parts of hexan-2-ol-5-one. The space-time yield is 39.8 g/cm³.h. The catalyst life is 130 days and the conversion is 98.7 percent.

EXAMPLE 3

The reaction is carried out as described in Example 1, using 500 parts per hour of butane-2,3-diol and 460 parts per hour of air, at 640° C. and 1.1 bar. The throughput is 1.6 t/m².h. 361 parts per hour of butane-2,3-dione are obtained, corresponding to a yield of 76% of theory, in addition to 35 parts per hour of butan-3-ol-2-one and 25 parts per hour of unconverted butane-2,3-diol. The catalyst life is 125 days and the conversion is 95 percent. The space-time yield is 57 g/cm³.h.

We claim:

1. A process for the preparation of a diketone of the formula I

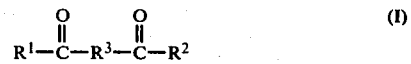

where $R^1$ and $R^2$ are identical or different and each is hydrogen or an aliphatic radical, $R^3$ is an aliphatic radical which may or may not be interrupted by —O— radicals and, if $R^1$ and/or $R^2$ is an aliphatic radical, may also be a single bond, by oxidizing a glycol with oxygen in the presence of a metal catalyst, wherein a glycol of the formula II

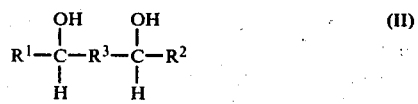

where $R^1$, $R^2$ and $R^3$ have the above meanings, is oxidized at from 450° to 750° C. in the presence of a catalyst bed consisting essentially of at least 2 layers of different particle size of silver crystals and/or copper crystals, at least one lower or rear layer, accounting for from 70 to 95 percent by weight of the catalyst, containing particles of size from 0.75 to 2.5 mm, whilst the remainder of the upper or front layers, accounting for from 5 to 30 percent by weight of the catalyst, contain particles of size from 0.1 to 0.75 mm.

2. A process as set forth in claim 1, wherein the reaction is carried out with a ratio of from 0.3 to 1.2 moles of oxygen per mole of starting material II.

3. A process as set forth in claim 1, wherein the reaction is carried out with a residence time of from 0.0005 to 0.2 second in the reaction chamber.

4. A process as set forth in claim 1, wherein the total thickness of the catalyst bed is from 10 to 50 mm.

5. A process as set forth in claim 1, wherein the reaction is carried out with a catalyst whereof the lower or rear layer(s) account s for from 80 to 90 percent by weight of all the catalyst particles and the upper or front layer(s) account s for from 10 to 20 percent by weight of all the catalyst particles.

6. A process as set forth in claim 1, wherein the reaction is carried out with a catalyst comprising from 3 to 7 layers.

7. A process as set forth in claim 1, wherein the reaction is carried out with 2 layers in the upper or front part of the bed, the first or upper layer accounting for from 0.5 to 29.5 percent by weight of the bed and containing particles of size from 0.1 to 0.4 mm and the second or lower layer accounting for from 0.5 to 29.5 percent by weight of the bed and containing particles or size from 0.4 to 0.75 mm.

8. A process as set forth in claim 1, wherein the reaction is carried out with 3 layers in the upper part of the bed, the layers accounting for the following proportions by weight of the total catalyst (the particle size being shown in parentheses): first or upper layer from 0.5 to 29 percent by weight (from 0.1 to 0.4 mm) second or middle layer from 0.5 to 20 percent by weight (from 0.4 to 0.6 mm) and third or lower layer from 0.5 to 29 percent by weight (from 0.6 to 0.75 mm).

9. A process as set forth in claim 1, wherein the reaction is carried out with 2 layers in the lower part of the bed, the layers accounting for the following proportions by weight (the particle size being shown in parentheses): first or upper layer from 5–90% by weight (from 0.75–1 mm) and second or lower layer from 5–90% by weight (from 1.00–2.5 mm).

10. A process as set forth in claim 1, wherein the reaction is carried out with 3 layers in the lower part of the bed, the layers accounting for the following proportions by weight (the particle size being shown in parentheses): first or upper layer from 5–85% by weight (from 0.75–1 mm), second or middle layer from 5–85% by weight (from 1–1.5 mm) and third or lower layer from 5–85% by weight (from 1.5–2.5 mm).

11. A process as set forth in claim 1, wherein the reaction is carried out with from 0.2 to 3 t of vaporous starting material II per m² of catalyst bed cross-section per hour.

12. A process as set forth in claim 1, wherein the reaction is carried out at from 500° to 700° C.

* * * * *